United States Patent
Bathurst et al.

(12)

(10) Patent No.: US 6,793,945 B2
(45) Date of Patent: Sep. 21, 2004

(54) AQUEOUS ANTI-APOPTOTIC COMPOSITIONS

(75) Inventors: Ian C. Bathurst, Laphayette, CA (US); Matthew W. Foehr, Santa Clara, CA (US)

(73) Assignee: Sky High, LLC, Evanston, IL (US)

( * ) Notice: Subject to any disclaimer, the term of this patent is extended or adjusted under 35 U.S.C. 154(b) by 0 days.

(21) Appl. No.: 10/040,572

(22) Filed: Jan. 4, 2002

(65) Prior Publication Data

US 2002/0155183 A1 Oct. 24, 2002

Related U.S. Application Data

(63) Continuation of application No. 09/479,431, filed on Jan. 7, 2000, now Pat. No. 6,413,556
(60) Provisional application No. 60/115,102, filed on Jan. 8, 1999.

(51) Int. Cl.[7] ............................................. A61K 35/78
(52) U.S. Cl. ....................................... 424/757; 514/867
(58) Field of Search ........................... 424/757; 514/867

(56) References Cited

U.S. PATENT DOCUMENTS

| 4,530,788 A | 7/1985 | Chang |
| 5,075,113 A | 12/1991 | DuBois |
| 5,635,187 A | 6/1997 | Bathurst et al. |
| 6,004,579 A | 12/1999 | Bathurst et al. |
| 6,413,556 B1 * | 7/2002 | Bathurst et al. ............. 424/757 |

FOREIGN PATENT DOCUMENTS

EP 0626177 A2 11/1994

OTHER PUBLICATIONS

Kumazawa et al., 1985. *Cancer Immunology Immuntherapy*, 19(2):79–84.

Bathurst et al., 1998, *Pharmaceutical Biology*, 36(2):111–123.

* cited by examiner

*Primary Examiner*—Christopher R. Tate
*Assistant Examiner*—Michele C. Flood
(74) *Attorney, Agent, or Firm*—Sheridan Ross P.C.

(57) ABSTRACT

The present invention provides methods for extracting anti-apoptotic compositions from various protein isolates and/or lipid mixtures with aqueous solutions not containing organic solvents. The compositions extracted by the methods can be used for a variety of purposes, including for therapeutic, nutritional and medicinal purposes.

2 Claims, 1 Drawing Sheet

*Fig. 1*

SEQUENCE LISTING

```
<160> NUMBER OF SEQ ID NOS: 13

<210> SEQ ID NO 1
<211> LENGTH: 7
<212> TYPE: PRT
<213> ORGANISM: Glycine max

<400> SEQUENCE: 1

Val Glu Lys Glu Glu Gln Asp
1               5

<210> SEQ ID NO 2
<211> LENGTH: 6
<212> TYPE: PRT
<213> ORGANISM: Glycine max

<400> SEQUENCE: 2

Val Glu Lys Glu Glu Gln
1               5

<210> SEQ ID NO 3
<211> LENGTH: 9
<212> TYPE: PRT
<213> ORGANISM: Glycine max
<220> FEATURE:
<221> NAME/KEY: misc_feature
<222> LOCATION: (1)..(9)
<223> OTHER INFORMATION: Xaa = any amino acid

<400> SEQUENCE: 3

Gly Glu Asp Glu Val Xaa Gln Ser Xaa
1               5

<210> SEQ ID NO 4
<211> LENGTH: 10
<212> TYPE: PRT
<213> ORGANISM: Glycine max
<220> FEATURE:
<221> NAME/KEY: misc_feature
<222> LOCATION: (1)..(10)
<223> OTHER INFORMATION: Xaa = any amino acid

<400> SEQUENCE: 4
```

```
Leu Lys Val Arg Glu Asp Xaa Asn Asn Pro
1               5                   10

<210> SEQ ID NO 5
<211> LENGTH: 10
<212> TYPE: PRT
<213> ORGANISM: Glycine max
<220> FEATURE:
<221> NAME/KEY: misc_feature
<222> LOCATION: (1)..(10)
<223> OTHER INFORMATION: Xaa = any amino acid

<400> SEQUENCE: 5

Ile Thr Ser Ser Lys Phe Asn Glu Xaa Gln
1               5                   10

<210> SEQ ID NO 6
<211> LENGTH: 10
<212> TYPE: PRT
<213> ORGANISM: Glycine max
<220> FEATURE:
<221> NAME/KEY: misc_feature
<222> LOCATION: (1)..(10)
<223> OTHER INFORMATION: Xaa = any amino acid

<400> SEQUENCE: 6

Phe Gly Glu Gln Ala Gln Gln Pro Asn Xaa
1               5                   10

<210> SEQ ID NO 7
<211> LENGTH: 10
<212> TYPE: PRT
<213> ORGANISM: Glycine max
<220> FEATURE:
<221> NAME/KEY: misc_feature
<222> LOCATION: (1)..(10)
<223> OTHER INFORMATION: Xaa = any amino acid

<400> SEQUENCE: 7

Phe Gly Glu Gln Ala Gln Gln Xaa Xaa Xaa
1               5                   10

<210> SEQ ID NO 8
<211> LENGTH: 8
<212> TYPE: PRT
<213> ORGANISM: Glycine max

<400> SEQUENCE: 8

Lys Lys Met Lys Lys Glu Gln Tyr
1               5

<210> SEQ ID NO 9
<211> LENGTH: 9
<212> TYPE: PRT
<213> ORGANISM: Glycine max
<220> FEATURE:
<221> NAME/KEY: misc_feature
<222> LOCATION: (1)..(9)
<223> OTHER INFORMATION: Xaa = any amino acid

<400> SEQUENCE: 9

Gly Ile Asp Glu Thr Ile Xaa Thr Met
1               5

<210> SEQ ID NO 10
<211> LENGTH: 9
<212> TYPE: PRT
```

-continued

```
<213> ORGANISM: Glycine max
<220> FEATURE:
<221> NAME/KEY: misc_feature
<222> LOCATION: (1)..(9)
<223> OTHER INFORMATION: Xaa = any amino acid

<400> SEQUENCE: 10

Gly Ile Asp Glu Thr Ile Xaa Thr Met
1               5

<210> SEQ ID NO 11
<211> LENGTH: 9
<212> TYPE: PRT
<213> ORGANISM: Glycine max
<220> FEATURE:
<221> NAME/KEY: misc_feature
<222> LOCATION: (1)..(9)
<223> OTHER INFORMATION: Xaa = any amino acid

<400> SEQUENCE: 11

Asp Phe Glu Leu Asn Asn Xaa Gly Xaa
1               5

<210> SEQ ID NO 12
<211> LENGTH: 8
<212> TYPE: PRT
<213> ORGANISM: Glycine max
<220> FEATURE:
<221> NAME/KEY: misc_feature
<222> LOCATION: (1)..(8)
<223> OTHER INFORMATION: Xaa = any amino acid

<400> SEQUENCE: 12

Glu Gly Lys Asp Glu Glu Xaa Ser
1               5

<210> SEQ ID NO 13
<211> LENGTH: 10
<212> TYPE: PRT
<213> ORGANISM: Glycine max
<220> FEATURE:
<221> NAME/KEY: misc_feature
<222> LOCATION: (1)..(10)
<223> OTHER INFORMATION: Xaa = any amino acid

<400> SEQUENCE: 13

Ile Ser Xaa Xaa Lys Leu Asn Glu Glu Gln
1               5                   10
```

AQUEOUS ANTI-APOPTOTIC COMPOSITIONS

CROSS REFERENCE TO RELATED APPLICATIONS

This application is a continuation of U.S. patent application Ser. No. 09/479,431, now U.S. Pat. No. 6,413,556, filed 7 Jan. 2000 which claims priority under 35 U.S.C. § 119(e) to U.S. Provisional Patent Application No. 60/115,102, filed on 8 Jan. 1999.

FIELD OF THE INVENTION

The present invention relates to novel compositions that are effective in inhibiting apoptotic cell death and to methods of preparing and using such compositions.

BACKGROUND OF THE INVENTION

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging.

Generally, cellular shrinkage, chromatin condensation, cytoplasmic blebbing, increased membrane, permeability and internucleosomal DNA cleavage characterize apoptotic cell death. Specific internucleosomal DNA fragmentation is a hallmark for many, but notably not all, instances of apoptosis. Apoptotic cell death appears to play a significant role in the tissue damage that occurs in association with various abnormal conditions, for example, ischemia, various gastrointestinal disorders, and organ transplantation.

Ischemia is the result of deceased blood flow to a particular area or organ of the body. Ischemia is responsible for several important types of physiologic damage such as brain damage, spinal cord trauma and myocardial ischemia. For example, recent data indicate that apoptosis plays a significant role in heart injury induced by ischemia and subsequent reperfusion. Severe cell damage during prolonged ischemia appears to result in necrotic death of myocardial cells. However, if the ischemia is relatively limited in extent and duration, the apoptotic pathway is initiated. Although early reperfusion decreases heart damage, massive cell death can occur with the restoration of blood flow. In this instance, the cells that die are those that remained viable at the end of ischemia Therefore, restoration of blood flow allows apoptosis to proceed. IGF and Calpain inhibitors, which are capable of preventing apoptosis in different systems, also inhibited apoptosis of cardiomyocytes following ischemia and reperfusion both in vito and in vitro.

As noted above, apoptosis has also been associated with various gastrointestinal disorders, including those caused by anticancer therapies. Gastrointestinal toxicity of anticancer therapies has been associated with the alteration of DNA metabolism and cell replication. In cancer patients, chemotherapy and radiotherapy damage cells and alter DNA metabolism and replication. These treatments not only kill rapidly dividing tumor cells, but also healthy stem cells in the intestinal crypts because of their rapid division. Destruction of mucosal cells by anti-cancer agents results in mucositis, stomatitis, diarrhea, decreased nutrient absorption, bacterial infections and anorexia. The dose of chemotherapy or radiation is often limited by these side effects.

Cancer patients can suffer from severe metabolic changes and mental stress resulting in cachexia and appetite loss. Common chemotherapy regimens can worsen these gastrointestinal disorders even further causing nausea and direct damage to epithelial cells. Careful consideration of the diet of patients can alleviate some of the destructive effects of chemotherapy. A variety of food supplements containing, in part, partially processed plant extracts have been used to ameliorate the gastrointestinal disorders that often accompany chemotherapy, radiation and AIDS. The supplements generally contain carbohydrates, fat and plant protein hydrolysates. Tomei and Cope et al., *Apoptosis The Molecular Basis of Cell Death* (Cold Springs Harbor Laboratory Press, 1991).

As shown in rat models, methotrexate treatment causes alterations of gastrointestinal mucosa leading to severe diarrhea, loss of appetite, and loss of weight in rats fed diets containing casein as the sole protein source. Previous experiments have demonstrated that rats fed a diet containing soy flour or isolated soy products experience a reduction in the incidence of these undesirable side-effects (Chevreau & Funk-Archuletta, *Toxicity of Chemotherapy*. pp. 269–295 (Grune & Stratton, N.Y., 1984); Funk & Baker, *J. Nutr.*, 121:1684–1692 (1991); Funk & Baker, *J. Nutr.*, 121:1673–1683 (1987)). A previously described anti-apoptotic fraction isolated from soy flour, referred to as soy-derived anti-apoptotic fraction (SDAAF), also referred to as AcE, for example, in U.S. Pat. No. 5,635,186), proved to be effective in alleviating methotrexate toxicity, which was confirmed by improved food intake, weight gain and absence of the diarrhea commonly observed following methotrexate injection in control animals fed casein based diets (Funk-Archuleta et al., *Nutrition and Cancer*, 29(3):217–221 (1991)).

The soy-derived anti-apoptotic fraction (SDAAF) reduces methotrexate toxicity likely by reduction of apoptosis (programmed cell death) (Funk-Archuletta et al., *Nutrition & Cancer, supra*). Methotrexate, similar to other chemotherapeutic agents and radiation treatment, increases the incidence of apoptosis in the areas of rapidly dividing cells, including gastrointestinal tract mucosa. Results from CX3H10T½ cell-based assay determined that SDAAF is a potent inhibitor of apoptosis (Funk-Archuletta et al., *Nutrition and Cancer, supra*, Tomei, et al., *Proc. Nat'l Acad. Sci (USA)*, 90:853–857 (1993)). It has also been reported that hydrolyzed soy protein products can decrease radiation-induced apoptosis in intestinal epithelial cells (Cope et al., *FASEB J.*, 5:a931 (1991)).

Plant-derived delipidated extracts that produce an anti-apoptotic effect are described in PCT Publication No. WO 95/15173, U.S. Pat. No. 5,567,425 and U.S. Pat. No. 5,635,186. These extracts, referred to as "AcE" in these references and as soy-derived anti-apoptotic fraction (SDAAF) herein, contain the phospholipids lysophosphatidic acid (LPA), lysophosphatidylcholine (LPC), lysophosphatidylinositol (LP), phosphatidic acid (PA) and phosphatidylinositol (PI) in addition to various protein and carbohydrate constituents.

Phospholipids are a class of amphipathic phosphorous-containing lipids that are essential constituents of biological membranes. Various phospholipid preparations have been used for cooking, drug delivery (liposomes), slow release delivery systems, carrier media for hydrophobic drugs, gene transfer and replacement therapy, sunscreens, emulsions, anti-foaming agents, replacement of damaged or absent pulmonary surfactants, detergents and membrane stabilization. PA, PI, LPC, LPI, and LPA are found in a variety of plant and animal products. LPA has been reported to have a variety of physiological activities including mitogenesis, growth factor, wound healing and as an anti-wrinkle agent. U.S. Pat. Nos. 4,263,286; 4,746,652; 5,326,690; 5,480,877; and 5,340,568. LPA is reviewed in detail by Moolenaar (1994) *TICB* 4:213–219; Eichholtz et al. (1990) *Biochem. J.* 291:677–680; and Moolenaar (1995) *J. Biol. Chem.* 270:12949–12952.

Several proteinase inhibitors derived from plant extracts have anticarcinogenic activity, including the Bowman-Birk Inhibitor. Birk (1985) *Int. J. Pep. Pro. Res.* 25:113–131. The Bowman-Birk Inhibitor is a disulfide bonded protein with a molecular weight of about 8 kD that can inhibit the activity of trypsin and chymotrypsin. This inhibitor has been found in crude soybean extracts and has been characterized immunologically. The Bowman-Birk Inhibitor has been found to suppress cellular transformation and have activity in degranulation of macrophages. The inhibitor is also known to increase pancreas size when fed to animals. The Bowman Birk Inhibitor, however, lacks anti-apoptotic activity.

In contrast, the compositions obtained from plant-derived extracts as described, for example, in U.S. Pat. No. 5,635,186, have anti-apoptotic activity. Accordingly, these compositions are unrelated to the Bowman Birk Inhibitor.

These anti-apoptotic compositions were generally prepared by extracting the aqueous solution from delipidated soybean powder to obtain an aqueous retentate in which the anti-apoptotic activity is soluble in a mixture of aqueous and organic solvent as described in U.S. Pat. No. 5,635,186. Although this earlier method is adequate, the present invention provides more efficient and cost effective methods of preparing compositions having anti-apoptotic activity.

SUMMARY OF THE INVENTION

The present invention provides methods for the aqueous extraction of anti-apoptotic compositions from protein isolates or lipid mixtures. The methods are generally accomplished by first mixing a protein isolate, a lipid mixture or a mixture thereof in an aqueous, non-organic solvent containing solution, and thereafter separating the aqueous solution from the insoluble material. Since the anti-apoptotic composition is soluble in the aqueous solution, the methods of the present invention provides a simple water extraction of the desired anti-apoptotic composition from the insoluble material. The extracted anti-apoptotic compositions can then be isolated from the aqueous solution by any means known in the art and, if desired, dried for various purposes.

Protein isolates useful as starting materials in the methods can be derived from plants, plant organs or plant extracts. Particularly suitable protein isolates are derived from plants of the leguminosae, solanum and allium families, especially soybeans. Useful lipid mixtures can be isolated from plant and animal tissues containing phospholipids or phosphatides, with one of the several lecithins being particularly useful, especially soybean-derived lecithins. Additionally, combinations of such protein isolates and lipid mixtures are useful in obtaining the anti-apoptotic compositions of the present invention. A ratio of 4:1 protein isolate to lipid mixture is particularly useful in the methods.

The present invention further provides the anti-apoptotic compositions produced by the water-extraction methods. The novel compositions can be used to treat or prevent an adverse condition associated with apoptosis, including, for example, gastrointestinal disorders, deleterious dermatological conditions, immunosuppression or immunodeficiency, reperfusion damage resulting from ischemia, cardiovascular disorders, transplantation, would healing, tissue rejection and Alzheimer's disease.

DETAILED DESCRIPTION OF THE INVENTION

The present invention is directed to compositions that inhibit apoptosis, and particularly to aqueous extracts of protein isolates and/or lecithin fractions having such activity. Such compositions obtained from soy protein isolates and/or soy lecithin fractions are referred to herein as Lexirin.

The compositions of the present invention are produced by novel methods generally accomplished by (a) mixing a protein isolate, a lipid mixture, or the combination of a protein isolate and lipid mixture in an aqueous, non-organic solvent containing solution; and (b) separating the aqueous solution from the insoluble material. The desired anti-apoptotic composition, which is water soluble, can then be extracted or isolated from the aqueous solution and further processed depending on the intended use.

A desirable feature of the present methods is that organic solvents are not used in the extraction step. As a result, the methods are cost efficient compared with known methods in which organic solvents are used.

For certain uses, the simple water extraction method of the present invention represents an advantage over the organic extraction methods in obtaining SDAAF as described in U.S. Pat. No. 5,635,186. For example, the present methods are more efficient and cost effective for large scale manufacturing since there is no need for organic solvents and the resulting organic waste disposal concerns.

In the present methods, the protein isolate can be obtained from any source known to those skilled in the art, including those sources described in U.S. Pat. No. 5,635,186, incorporated herein by reference. Such sources include a variety of plants and plant organs. Plants in the leguminosae families are particularly useful, especially soybeans. Soy protein isolates derived from soybeans are also commercially available, such as the heat-treated soy protein isolate sold under the trademark Ardex® D (Serial #066–901, Archer Daniels Midland Co., Decateur, Ill.), which is particularly suitable for use in obtaining the Lexirin compositions. Other suitable protein isolates/extracts include Ardex®F, Ardex®F dispersible, Ardex®FR, Ardex®R, Nutrisoy® and Pro-Fam® (all from Archer Daniels Midland Co.), as well as protein fractions sold as Response®, Promine®, Promax®, Procon® and Centrex® (all from Central Soya, Ft. Wayne, Ind.). However, the present compositions can be isolated from other plants, such as those in the potato, pea and garlic families. Accordingly, any plant, plant extract or plant organ that yields the anti-apoptotic compositions is suitable for use in the present invention. The present compositions can vary slightly in chemical constituents depending on the source and growing conditions of the plant from which they are derived. Protein extracts that contain a profile similar to that of the Ardex® family are also contemplated and can be readily identified by those skilled in the art.

As noted above, the lipid mixture can be mixed alone with water or combined with a protein isolate. The term "lipid mixture" refers to the phospholipid or phosphatide fraction of substances as well as glycerols and free fatty acids. Such lipid mixtures occur widely in nature and can be isolated from both plant and animal tissues according to methods well known in the art. Preferably, the lipid mixture is lecithin, and more preferably lecithin containing soy lipids and free fatty acids. Oil or solid lecithins (in granulated or blocked for, also referred to as "structured lecithins") are also suitable. Lecithins derived from soybeans are commercially available, including a product sold under the trademark Centrolex® (Central Soya Co., Fort Wayne, Ind.). Other suitable lecithin fractions include Centrol®, Centrophase®, Blendmax®, Centrolene® (all from Central Soya). Lecithin fractions that contain a profile similar to that of Centrolex® are also contemplated and can be readily identified by those skilled in the art.

Although any therapeutic ratio of protein isolate to lipid mixture is useful, a ratio of 4:1 (protein isolate:lipid mixture) has been found to be particularly useful. Each component is dissolved in water at an appropriate concentration to obtain the desired ratio. Any type of water (for example, tap, distilled, deionized water for injection (WF1) and the like) can be used to prepare the aqueous solution in the present methods.

Mixing the protein isolate and/or lipid mixture in the aqueous solution can be accomplished by any means known in the art, including, agitating, shaking, aeriating, blending, stirring and the like. The components are mixed for a sufficient time to produce an even dispersion, preferably at least five minutes. Temperature is also not a critical factor provided it is does not denature the proteins. Generally, a temperature of up to about 45° C. can be used, although room temperature (25° C.) is preferred for convenience of manufacturing.

The resulting supernatant containing the anti-apoptotic compositions can be separated from the insoluble material by any means known in the art. For example, the aqueous mixture can first be centrifuged and then filed or decanted to isolate the aqueous extract from the insoluble material.

The aqueous extract can then be used as is or can be further processed depending on the intended use. Further processing can include sterilization according to methods known in the art, including, for example, gamma radiation treatment or sterile filtering. If desired, the aseptic or non-aseptic aqueous extract can then be dried by any method known in the art, including vacuum drying, air drying, spray drying or freeze-drying (lyophilization). The dried composition can be capleted or tableted for intended use under non-sterile conditions and can later be gamma-irradiated if sterility is desired. Those skilled in the art can readily determine the appropriate drying method depending on the intended use. The aqueous extract can be stored for months in sterile solution and indefinitely as a dried solid.

After drying, the dried compositions can then be resuspended in an appropriate buffer. A wide range of pH values are effective. Preferably, the pH of the buffer is between 5.5–8 although, any pH at which the composition is at least minimally effective is suitable for use. A mixture having pH 8.0 is particularly useful. For example, the anti-apoptotic compositions can be suspended in 50 mM ammonium bicarbonate in 0.154 M sodium chloride, 250 μM EDTA with a pH of 7.7–8.0. The buffer can be a physiologically acceptable carrier for use in therapeutic or nutritional applications. As used herein, the term "physiologically acceptable carrier" refers to a solution that does not cause an adverse physical reaction upon administration and one in which the Lexirin compositions are sufficiently soluble.

Alternatively, the dried composition can be resuspended in an appropriate culture medium for culturing cells in vitro.

The compositions can be suspended in any buffered solution having a pH range of 2–10, more preferably, about 4–8 and most preferably about 6–8. Suitable buffers include, but are not limited to , D-PBS (phosphate buffered saline, GibcoBRL) or 50 mM ammonium bicarbonate containing isotonic sodium chloride.

After resuspending in an appropriate buffer, the composition can be sonicated, sterilized and used as desired.

The dried compositions of the present invention can also be mixed with other physiologically acceptable and ingestable ingredients. For example, the dried compositions can be mixed with edible ingredients for use as a nutritional supplement or medical food. The resulting mixture can be in any ingestable form, including, for example, as a food bar or as a powder that can be mixed with a liquid, such as, for example, water, milk or juice, to form a solution or cocktail.

As noted above, a preferred composition of the present/or a soy-derived lecithin invention is an aqueous soy extract of a soy protein isolate and having anti-apoptotic activity, referred to herein as Lexirin. This preferred Lexirin composition contains the following phospholipids: phosphatidylcholine, phosphatidylethanolamine, phosphatidic acid, phosphatidylinositol, lysophosphatidylcholine. Lexirin also contains monoacylglycerol, diacylglycerol, and free fatty acids. The proteins in Lexirin have also been partially sequenced and characterized as described in Example 2 and the results shown in Table 2 and 3. Differences between Lexirin and SDAAF are shown, for example, in Table 3 and FIG. 1. Lexirin comprises by total weight about 35 to 555 protein, about 15 to 30% phospholipid, and less than about 10% carbohydrate.

The compositions of the present invention can be used for any of the uses described herein and in U.S. Pat. No. 5,635,186 and Funk-Archuleta et al., *Nutrition and Cancer*, 29(3):217–221 (1997), both incorporated herein by reference. Other intended uses are as described in U.S. Pat. No. 5,635,186, U.S. Pat. No. 5,635,187, U.S. Pat. No. 5,567,425, U.S. Pat. No. 5,624,672, U.S. Pat. No. 5,620,885, and. U.S. Pat. No. 5,759,548, all incorporated herein by reference.

Accordingly, the present invention further relates to methods of treating or preventing conditions associated with adverse effects of apoptosis. These methods are generally accomplished by administering a therapeutically effective amount of the anti-apoptotic compositions of the present invention. Conditions that can be treated according to the methods of the present invention include, for example, various gastrointestinal disorders, deleterious dermatological conditions, immunosuppression or immunodeficiency, reperfusion damage resulting from ischemia, cardiovascular disorders, rejection of tissue, cell or organ transplantation, wound healing and Alzheimer's disease.

Gastrointestinal perturbations include, but are not limited to, damage to the intestinal mucosa, severe chronic ulcers, colitis, radiation-induced damage, parasite-induced damage, gastroenteritis and diarrhea from any other cause. Various viral and bacterial infections are known to result in gastrointestinal perturbations, including, for example, immunosuppressive viruses. The present compositions are also suitable for use in treatment of the side effects associated with these infections.

The present compositions are also suited for use in ameliorating the gastrointestinal disturbances associated with chemotherapy. As previously shown, rats treated with methotrexate and fed diets containing specific soy fractions suffered less feeding problems and had none of the diarrhea found in the control animals. Thus, the compositions of the present invention are suitable for use not only in preventing the weight loss and diarrhea associated with chemotherapy, but also the accompanying nausea.

Damage to the intestinal mucosa not only occurs in methotrexate-treated or radiation-treated animals, but also in infants with gastroenteritis and patients infected with HIV. In experimental animal models, methotrexate-induced diarrhea was relieved when rats received soy-based animal feed. In several studies of infants with diarrhea, diarrhea episodes were shorter in the groups who were fed formulas containing hydrolysate. These findings suggest that soy proteins exert a protective effect on the intestinal mucosa, and relieve diarrhea.

In humans, administration can be by any method known in the art of gastrointestinal administration. Preferably, administration is oral.

The present compositions are further suited for the treatment of various gastrointestinal conditions in animals, including livestock such as cattle. Such conditions, particularly diarrhea, account for the loss of many calves. Treatment of gastrointestinal conditions is preferably by gastrointestinal administration. In the case of cattle, an effective amount of the present compositions can be conveniently mixed in with the feed.

In addition, the present compositions can be administered to inmmunodeficient patients, particularly HIV-positive patients, to prevent or at least mitigate apoptotic death of T cells associated with the condition, which results in the exacerbation of immunodeficiencies as seen in patients with AIDS.

The invention can also be used as a topical treatment of the skin to prevent or inhibit hair loss. Hair loss has been shown to be associated with apoptosis of the hair follicle cells. Stenn et al., *J. Invest. Dermatol.* 103:107–111 (1994).

As used herein, the term "therapeutically effective amount" refers to an amount sufficient to effect a beneficial or desired therapeutic result and depends in part on the route of administration, the indication to be treated and other criteria readily determined by those skilled in the art. Typically, a therapeutically effective amount is one sufficient to modulate apoptosis in the condition being treated as evidenced by histological analysis or amelioration of the symptoms compared to a control. As a dietary supplement, for example, the preferable dose is in the range of about 0.1%–10% of dietary intake.

The compositions of the present invention can also include pharmaceutically acceptable excipients. Pharmaceutically acceptable excipients include, but are not limited to, topical pharmaceutically acceptable carrier, cosmetic carrier, sterile solutions, sterile isotonic solutions, ingestable liquids and/or solids, pharmaceutically acceptable aerosols and solutions for organ/tissue/cell preservation and/or transplantation such as, for example, polyethylene glycol.

In addition, the compositions of the present invention can also include other therapeutic agents. Suitable classes of such therapeutic agents include, for example, drugs, antibiotics, toxins, antibodies, wound healing agents, antioxidants and dietary supplements for nutritional and medicinal purposes.

Suitable drugs that can supplement the present compositions include, but are not limited to, antipyretic and antiinflammatory drugs, analgesics, antiarthritics, antispasmodics, antidepressants, antipsychotics, tranquilizers, antianxiety drugs, narcotic antagonists, antiparkinson agents, cholinergic antagonists, chemotherapeutic agents, immunosuppressive agents, antiviral agents, parasiticides, appetite suppressants, antiemetics, antihistamines, antimigraine agents, coronary vasodilators, cerebral vasodilators, peripheral vasodilators, hormonal agents, contaceptives, antithrombotic agents, diuretics, antihypertensive agents, cardiovascular drugs, opiods, and vitamins are all included in the compositions described herein.

For example, cardiac glycosides include digitalis, digitoxin, lanatoside C, and digoxin, while useful antiarrhythmic agents include propanolol, etanolol, verpamil, captopril, and isosorbide. Useful immunotherapeutics include interferon, interleukins, particularly interleukin-2, monoclonal antibodies, and gammaglobulin. Useful antifungal drugs include amphotericin B, myconazole, muramyl dipeptide and clotrimazole. Anticancer agents that can be included in the present compositions include, for example, azathioprine, bleomycin, byclophosphamide, adriamycin, daunorubicin, and vincristine. Steroids that can be added include prednisone, triamicinolone, hydrocortison, dexamethasone, betamethasone, and prednisolone.

Useful hormones include, for example, antidiuretics, corticosteroids, testosterone, estrogen, thyroid hormones, growth hormones, ACTH, progesterone, gonadotropin, and mineralocorticoid. Examples of suitable antihistamines include pyribenzamine, chorpheniramine, and diphenhydramine. Suitable antiparasitic agents include, for example, praziquantel, metronidazole and pentamidine, while suitable antiviral agents include, for example, acyclovir and derivatives, WinthropO-51711, ribavirin, rimantadine/amantadine, azidothymidine and derivatives, adenine arabinoside and amidine-type protease inhibitors.

Vaccines can also be included in the compositions, including, for example, vaccines for influenza, respiratory synchythial virus and Hemophilus influenza.

Other suitable drugs include antihypotension drugs (for example, dopamine and dextroamphetamine), antiasthma drugs (for example, metaproterenol, aminophylline, theophylline, terbutaline, Tegretol, ephedrine, isoproterenol, adrenaline and norepinephrine), antihypertensive drugs (for example, apresoline and etanolol), sedatives and analgesics (for example, morphone, dilaudid, codeine, codeine-like synthetics, Demerol, oxymorphone, phenobarbital, barbiurates and over-the-counter analgensics such as aspirin, ibuprofin and the like), tranquilizers (for example, chlorpromazines, benzodiaepine, butyropheomes, hydroxyzines, meprobamate, phonothiazines, reserpine, and thioxanthines), antidiabetics (for example, diabenese and insulin) and other pharmaceuticals (for example, receptor agonists and antagonists).

Suitable antibiotics include, for example, ampicillin, tetracycline, chloramphenicol, erthromycin, amphotericin B, penicillin, cephaothin, imipenem, cefofaxime, carbenicillin, vancomycin, gentamycin, tobramycin, piperacillin, moxalactam, amoxicillin, cefazolin, cefadroxil, cefoxitin, other aminoglycosides and other cephalosporins. Suitable wound healing agents include, for example, transforming growth factors, platelet-derived growth factors, epidermal growth factors and fibroblast growth factors. Suitable antioxidants include, but are not limited to, naturally-occurring antioxidants such as tocopherols, (for example, α-tocopherol, vitamin E), ascorbic acid (vitamin C), β-carotene (vitamin A), dihydrolipoamide, flavenoids, synthetic antioxidants such as butylated hydroxytoluene, butylated hydroxyanisole, propyl gallate, other phenolic antioxidants and phenothiazines, and chelators such asdesferroxamide, HBED and CP130.

Routes of administration include, but are not limited to, oral, topical, transdermal and gastrointestinal. Topical administration is accomplished via a topical applied cream, gel, rinse and the like containing a therapeutically effective amount of the present compositions.

While the present compositions can be topically administered alone, it may be desirable to administer them in a mixture with a pharmaceutically or cosmetically acceptable topical carrier. "Pharmaceutically acceptable topical carrier" as used herein is any substantially non-toxic carrier conventionally useable for topical administration of pharmaceuticals in which the present compositions remain stable and bioavailable when applied directly to skin or mucosal surfaces. For example, the compositions can be dissolved in a liquid, dispersed or emulsified in a medium in a conventional manner to form a liquid preparation or mixed with a semi-solid (gel) or solid carrier to form a paste, powder, ointment, cream, lotion or the like.

Suitable topical pharmaceutically acceptable carriers include water, petroleum jelly, petrolatum, mineral oil, vegetable oil, animal oil, organic and inorganic waxes, such as microcystalline, paraffin and oxocerite wax, natural plymers, such as xanthanes, gelatin, cellulose, collagen, starch, or gum arabic, synthetic polymers, such as discussed below, alcohols, polyols, and the like. The carrier may be a water miscible carrier composition that is substantially miscible in water. Such water miscible pharmaceutically acceptable topical carrier composition can include those made with one or more appropriate ingredients set forth above and can also include sustained or delayed release carriers, including water containing, water dispersible or water soluble compositions, such as liposomes, microsponges, microspheres or microcapsules, aqueous base ointments, water-in-oil or oil-in-water emulsions, gels or the like.

In one embodiment of the invention, the pharmaceutically acceptable topical carrier comprises a sustained release or delayed release carrier. The carrier is any material capable of sustained or delayed release of the present compositions to provide a more efficient administration resulting in one or more of less frequent and/or decreased dosage of the compositions, ease of handling, and extended or delayed effects on dermatologic conditions. The carrier is capable of releasing the compositions when exposed to any oily, fatty, waxy, or moist environment on the area being treated or by diffusing or by release dependent on the degree of loading of the present compositions to the carrier in order to obtain releases of such compositions. Non-limiting examples of such carriers include liposomes, microsponges, microspheres, or microcapsules of natural and synthetic polymers and the like.

Examples of suitable carriers for sustained or delayed release in a moist environment include gelatin, gum arabic, xanthane polymers. Example of suitable carriers by degree of loading include lignin polymers and the like, while suitable carriers in oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. Preferably, the sustained or delayed release carrier is a liposome, microsponge, microsphere or gel.

The compositions used in the method of treating dermatologic conditions of the invention are applied directly to the areas to be treated. While not required, it is desirable that the topical composition maintain the present compositions at the desired location for about 24 to 48 hours.

If desired, one or more additional ingredients conventionally found in topical pharmaceutical or cosmetic compositions can be included with the carrier, such as a moisturizer, humectants, odor modifier, buffer, pigment, preservative, Vitamins such as A, C and E, emulsifier, dispersing agent, wetting agent, odor-modifying agent, gelling agents, stabilizer, propellant, antimicrobial agents, sunscreen, enzymes and the like. Those of skill in the art of topical pharmaceutical formulations can readily select the appropriate specific additional ingredients and amounts thereof. Suitable non-limiting examples of additional ingredients include superoxide dismutase, stearyl alcohol, isopropyl myristate, sorbitan monooleate, polyoxyethylene stearate, propylene glycol, water, alkali or alkaline earth lauryl sulfate, methylparaben, oxtyl dimethyl-p-amino benzoic acid (Padimate O), uric acid, reticulin, polymucosaccharides, hyaluronic acids, aloe vera, lecithin, polyoxyethylene sorbitan monooleate, polyethylene glycol, vitamin A or C, tocopherol (vitamin E), alpha-hydroxy of alpha-keto acids such as pyruvic, lactic or glycolic acids, or any of the topical ingredients disclosed in U.S. Pat. Nos. 4,340,586, 4,695,590, 4,959,353 or 5,130,298 and 5,140,043.

Because dermatologic conditions to be treated may be visible, the topical carrier can also be a cosmetically acceptable topical carrier. By "cosmetically acceptable topical carrier" as used herein is meant any substantially non-toxic carrier conventionally used for topical administration of cosmetics in which the present compositions will remain stable and bioavailable when applied directly to the skin surface. Suitable cosmetically acceptable carriers are known to those of skill in the art and include, but are not limited to, cosmetically acceptable liquids, creams, oils, lotions, ointments, gels, or solids, such as conventional cosmetic night creams, foundation creams, suntan lotions, sunscreens, hand lotions, make-up and make-up bases, masks and the like. Thus, to a substantial extent cosmetically acceptable topical carriers and pharmaceutically acceptable carriers are similar, if not often identical, in nature so that most of the earlier discussion on pharmaceutically acceptable carriers also applies to cosmetically acceptable carriers. The compositions can contain other ingredients conventional in cosmetics including perfumes, estrogen, Vitamins A, C or E, alpha-hydroxy or alpha-keto acids such as pyruvic, lactic or glycolic acids, lanolin, Vaseline, aloe vera, methyl or propyl paraben, pigments.

The effective amount of the anti-apoptotic compositions of the present invention used to treat dermatologic conditions or diseases can vary depending on such factors as condition of the skin, age of the skin, the type of formulation and carrier ingredients used, frequency of administration, overall health of the individual being treated and the like. The precise amount for any particular patent use can be determined by those of skill in the pharmaceutical art taking into consideration these factors and the present disclosure. Preferably the composition is administered in at least two doses and no more than about six doses per day, or less when a sustained or delayed release form is used.

The invention further encompasses solutions for inhibiting apoptosis in mammalian organs, tissues or cells during their surgical removal and/or handling prior to transplantation. These mammalian organs, tissues or cells can be from human or other mammalian sources, such as pigs, sheep and the like. In addition, insect cells can also be used for transplantation under suitable situations readily determined by those skilled in the art. These organs, tissues or cells can be used for autotransplantation or xenotransplantation. The solutions, which contain the anti-apoptotic compositions of the present invention, can be used to flush, perfuse and/or store the organs, tissues or cells. In all cases, effective concentrations of such compositions can be readily determined by those skilled in the art and with the guidance provided, for example, in U.S. Pat. No. 4,938,961, entitled "Organ Preservation Solution containing Polyethylene Glycol and method of Performing Cardioplegia," incorporated herein by reference.

In a further embodiment, the present compositions can also be used for cardioplegia in cardiac bypass surgery. General guidance for performing cardioplegia is provided in U.S. Pat. No. 4,938,961, incorporated herein by reference.

The invention further provides methods of limiting and preventing apoptosis during the culture of cells by the addition of an effective amount of the present compositions in any media or solutions used in the art of culturing cells. The cells can be derived from mammals, including humans, or insects. An effective amount of the anti-apoptotic compositions is one which decreases the rate of apoptosis and/or preserves the cells. The compositions of the present invention can limit or prevent apoptosis under circumstances in which cells are subjected to mild traumas which would normally stimulate apoptosis. Such traumas can include, for example, low level irradiation, thawing of frozen cell stocks, rapid changes in the temperature, pH, osmolarity, or ion concentration of culture media, prolonged exposure to non-optimal temperature, pH, osmolarity, or ion concentration of the culture media, exposure to cytotoxins, disassociation of cells from an intact tissue in the preparation of primary cell cultures, serum deprivation (or growth in serum-free media).

Accordingly, the invention encompasses compositions comprising tissue culture medium and an effective amount of the present anti-apoptotic compositions. Serum-free media to which the present compositions can be added as anti-apoptotic media supplements include, but are not limited to, AIM V® Media, Neuman and Tytell's Serumless Media, Trowell's T8 Media, Waymouth's MB 751/1 and 705/1 Media, and Williams' Media E. Additional serum-free media suitable for cell culture include Basal Media Eagle's, Fischer's Media, McCoy's Media, Media 199, RPMI Media 1630 and 1640, Media based on F-10 & F-12 Nutrient Mixtures, Leibovitz's L-15 Media, Glasgow Minimum Essential Media, and Dulbecco's Modified Eagle Media. The cell culture media supplemented with the present anti-apoptotic compositions can also be supplemented with any media supplement known in the art, including, but not limited to, sugars, vitamins, hormones, metalloproteins, antibiotics, antimycotics, growth factors, lipoproteins and sera.

The ability to prevent apoptosis in cultured cells have an infinite number of industrial and research purposes. In one embodiment, such cultured cells can be used for cell transplantation, either for autotransplantation or xenotransplantation by methods known in the art.

The following examples are intended to illustrate, but not limit, the present invention.

EXAMPLE 1

Preparation of the Diet Supplements

A. Soy-derived Anti-apoptotic Fraction (SDAAF)

The soy-derived anti-apoptotic fraction (SDAAF) was prepared as previously described by Funk-Archuleta, et a., *Nutrition and Cancer, supra*. Briefly, soy flour, type 1, unheated (Sigma, St. Louis, Mo.) was defatted by stirring at room temperature for 30 minutes in 70% acetone (2×weight/volume). The defatted soy flour was recovered by low speed centrifugation, and the desired fraction was then extracted into 50% ethanol (equal weight/volume) by stirring at room temperature for 60 minutes. The extracted material was recovered by low speed centrifugation followed by concentration over a 10 kD ultrafiltration membrane (Filtron, Northborough, Mass.). The concentrated material was then freeze-dried and the resultant powder referred to as soy-derived anti-apoptotic fraction (SDAAF).

B. Soy Water Extract (Lexirin)

A heat-treated soy protein isolate (40 g/L) (Archer Daniels Midland, Decatur, Ill.) and soy lecithin (10 g/L) (Central Soya, Fort Wayne, Ind.) were dissolved in de-ionized water and stirred at room temperature for 60 minutes at 1000 rpm using a laboratory mixer (Caframo, Ontario, Canada). Following mixing, the suspension was centrifuged at room temperature for 25 minutes at 4000 rpm. The supernatant was then decanted and freeze-dried and the resultant powder referred to as Lexirin.

Lexirin extraction yields manufactured at various scales were determined. Table 1 shows the results of the various process scales.

TABLE 1

Lexirin Extraction Yields at Various Scales

| Process Scale | Lexirin Yield | g/L Yield |
|---|---|---|
| 0.1 L | 1.85 g | 18.5 |
| 10 L | 201.6 (± 18.5) g | 20.1 |
| 2,500 L | 61.44 Kg | 24.5 |

C. Soy Flour

Soy flour, Type 1 (Sigma, St. Louis, Mo.) containing approximately 52% protein was used as the soy flour diet supplement. The soy flour used was an unheated and defatted flour derived from Glycine-max soy.

D. Casein

Vitamin-free casein (Sigma, St. Louis, Mo.) was used in the control diet.

EXAMPLE 2

Characterization of Lexirin

A. Protein Content of Lexirin

Soy proteins present in the Lexirin extract were analyzed by sodium dodecyl sulfate polyacrylamide gel electrophoresis (SDS-PAGE) under reducing conditions and transferred to a polyvinylidene difluoride (PVDF) membrane by immunoblotting using a 10 mM $KH_2PO_4$, 0.05% SDS buffer, pH 8.0. Proteins were stained with 0.1% Coomassie blue R250 in 40% methanol, 1% acetic acid for 1 minute and destained with 50% methanol. Protein bands visible after staining were excised from the membrane and their amino termini sequenced through 10 amino acid residues on an Applied Biosystems (Foster City, Calif.) model 476A pulsed liquid phase protein sequencer.

As shown in Table 2, the protein composition of Lexirin consisted of 12 bands identifiable by staining with Coomassie blue R250. All bands yielded sequence information. The two bands of highest molecular weight (bands 1 and 2) yielded the same amino-terminal sequence and are likely identical proteins differing in post-translational modification or carboxy-terminal processing. This also applies to bands 6 and 7 and bands 9 and 10. Of the identifiable sequences, four were homologous with conglycinin or glycinins (bands 4, 5, 9, and 10) and 1 with a putative thiol protease precursor (band 8).

TABLE 2

Amino Terminal Sequencing of Protein Content of Lexirin

| Band Number | Approximate Molec. Wt. (kDa) | Amino Terminal Sequence | SEQ.ID.NOS. |
|---|---|---|---|
| 1 | 80 | V-E-K-E-E-Q-D | SEQ.ID.NO.1 |
| 2 | 80 | V-E-K-E-E-Q | SEQ.ID.NO.2 |
| 3 | 66 | G-E-D-E-V-X-Q-S-X | SEQ.ID.NO.3 |
| 4 | 47 | L-K-V-R-E-D-X-N-N-P | SEQ.ID.NO.4 |
| 5 | 40 | I-T-S-S-K-F-N-E-X-Q | SEQ.ID.NO.5 |
| 6 | 39 | F-G-E-Q-A-Q-Q-P-N-X | SEQ.ID.NO.6 |
| 7 | 34 | F-G-E-Q-A-Q-Q-X-X-X | SEQ.ID.NO.7 |
| 8 | 32 | K-K-M-K-K-E-Q-Y | SEQ.ID.NO.8 |
| 9 | 25 | G-I-D-E-T-I-X-T-M | SEQ.ID.NO.9 |
| 10 | 22 | G-I-D-E-T-I-X-T-M and | SEQ.ID.NO.10 |
|   |   | D-F-E-L-N-N-X-G-X | SEQ.ID.NO.11 |
| 11 | 15 | E-G-K-D-E-E-X-S | SEQ.ID.NO.12 |
| 12 | 13 | I-S-X-X-K-L-N-E-E-Q | SEQ.ID.NO.13 |

The amino terminal sequences were further characterized for each band. For bands 1 and 2, the amino terminal sequences are unknown, but likely proteolytically modified forms of the same unknown protein. For bands 3, 10 and 11, the amino terminal sequences were also unknown, but likely proteolytically modified form of the same unknown protein. For bands 3, 10 (SEQ.ID.NO.10), 11 and 12 the sequences are of unknown identity. The amino terminal sequences for the following bands are the same as known proteins identified in parenthesis: band 4 (beta conglycinin), band 5 (glycinin 5), band 8 (P34 probable thiol protease precursor), band 9 (glycinin precursor), and band 10 SEQ.ID.NO.10 (glycinin precursor). All proteins are of soybean origin.

B. Protein, Sugar and Phosphate Concentrations of Lexirin and SDAAF.

Protein (by BCA method), total sugar (by orcinol method), and total phosphate (molybdenum method) of SDAAF and Lexirin are provided in Table 3. Values are the average for three separate lots. The total protein percent was determined with a kit (catalog #23223/23224) available from Pierce Chemical Co. (Rockford, Ill.), which is described in U.S. Pat. No. 4,839,295. The percent total sugar was determined by the method described in Chaplin & Kennedy, *Carbohydrate Analysis—A Practical Approach*, p.38 (IRL Pres, Washington, D.C. 1986). Finally, the percent totally phosphate was determined by the method described in Christie, *HPLC and Lipid: A Practical Guide*, p. 132 (Pergamon Press, N.Y. 1987).

TABLE 3

| Fraction | % Total Protein | % Total Sugar | % Total Phosphate |
|---|---|---|---|
| SDAAF | 47.5 (± 4.2) | 2.3 (± 0.8) | Not tested |
| Lexirin | 41.0 (± 2.1) | 8.1 (± 1.8) | 22.3 (± 9.5) |

EXAMPLE 3

Trypsin Inhibition Assays

Enzyme inhibition assays were performed using p-nitroanilidine substrates (Sigma, St. Louis, Mo.) for trypsin (Abramovitz, et al., *J. Bol. Chem.*, 258:15153–15157 (1983), incorporated herein by reference). Samples tested at various concentrations were pre-incubated with enzyme for five minutes prior to the addition of substrate (arginine-p-nitroanilide). Substrate concentration was kept constant at 1.0 mM. Absorbance was measured at 405 nm and percent of enzyme activity was calculated at each concentration as compared to controls.

Figure 1:
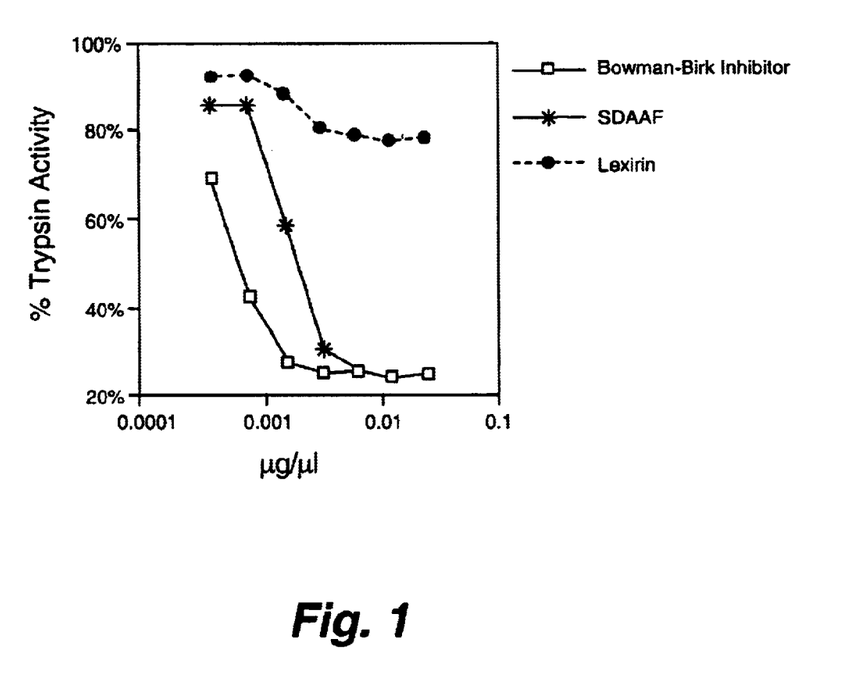
FIG. 1 graphically depicts the results of the trypsin inhibition assay. Various doses of Bowman-Birk Inhibitor, SDAAF, and Lexirin were tested using a p-nitroanilide substrate for trypsin as described in Abramovitz et al., *J. Biol. Chem.* 258:15153–15157 (1983)

As shown in FIG. 1, trypsin activity was reduced to 24% of control at doses of $6.25–25.0\times10^{-3}$ μg/μl of Bowman-Birk Inhibitor or SDAAF. Equal doses of Lexirin decreased trypsin activity only to 8% of control values.

EXAMPLE 4

C3H10T½ Cell Apoptosis Bioassay

The C3H10T½ cell apoptosis assay was performed as described in U.S. Pat. No. 5,637,486, incorporated herein by reference and Funk-Archuletta, et al. *Nutrition and Cancer*, supra. Briefly, mouse embryonic C3H10T½ cells (clone 8), obtained from ATCC (Rockville, Md.) were maintained in exponential growth phase where cell cycle is randomly distributed and no cells are arrested in $G_0$. Cells were seeded five days prior to the initiation of the assay in 60 mm petri dishes at $1–2\times10^3$ cells per milliliter in Basal Media Eagle (BME) (Gibco, Grand Island, N.Y.) supplemented with 10% fetal calf serum (Hyclone, Logan, Utah). The media was changed 48 hours prior to the start of the experiment. At time zero the cells were typically 60–90% confluent and the media was replaced with serum-free BME media and sterile-filtered. Controls included the addition of $5\times10^{-8}$M 12-O-tetradecanoyl phorbol-13 acetate (TPA) (Sigma, St. Louis, Mo.) to ensure the responsiveness of the cells to an anti-apoptotic signal. Fatty Acid Free Bovine Serum Albumin (Boehringer Mannheim, Indianapolis, Ind.) was included as a protein control. TPA was stored at a concentration of $10^{-3}$M in acetone and diluted in BME to the desired doses. All assays were made in triplicate and analysis of the cells were made 18 to 24 hours following serum deprivation and test sample addition. All samples were tested at 100 μg/mL assay media.

Two parameters were analyzed in each culture dish. All non-adherent or loosely adherent cells were removed from the culture dish and measured by counting in an electric particle counting instrument (Coulter, Hialea, Fla.). These serum deprived release (SDR) cells are defined as the apoptotic cells, and are released in response to cultivation in serum-free media. Approximately 90% of the SDR cells have been proven to be apoptotic as shown by typical apoptotic markers including ultrastructure and DNA fragmentation analysis as described in Tomei et al., *Proc. Nat'l Acad. Sci. (USA)*, supra. The remaining adherent cells were exposed to Hank's balanced salt solution without calcium and magnesium salts containing trypsin (0.05%) and EDTA (0.53 mM). ADH cells were incubated with the trypsin/EDTA solution for 10 minutes at room temperature on a rocking platform. Following incubation, the cells were removed and measured in the electric particle counter as described above.

Antiapoptotic activity of the various diet supplements are described in Table 4. All of the diet supplements exhibited antiapoptotic activity as compared to controls. Following 24 hours of serum deprivation, the raw soy four, SDAAF and Lexirin treated cultures had 56.2, 60.5, and 83.6% viable cells respectively. Control cultures contained only 29.8% viable cells. Casein treatment resulted in 63.2% viable cells; however, this activity can likely be attributed to the presence of IGF2, which is commonly found in many casein preparations. IGF2 is a mitogen that can mask the serum deprivation-induced apoptotic response in C3H1051/2 cells. Fatty Acid Free Bovine Serum albumin showed no activity (29% viable cells).

TABLE 4

| Test Sample | % Viable (Adherent) Cells (± SD) |
|---|---|
| Control | 29.8 (± 3.7) |
| Bovine Serum Albumin (Fatty Acid Free) | 29.0 (± 2.0) |
| Casein | 63.4 (± 3.6) |
| Raw Soy Flour | 56.2 (± 3.9) |
| SDAAF | 60.5 (± 0.2) |
| Lexirin | 83.6 (± 1.0) |

Small scale (100 mL) extraction yields and anti-apoptosis activity using various ratios of protein isolate:lecithin were tested. Post-water extraction weight yield (at 100 mL scale) and 10T½ cell anti-apoptosis activity (expressed as percent of viable cells) for extracts from various ratios of protein isolate:lecithin are shown in Table 5.

TABLE 5

| Ratio of Protein Isolate: Lecithin prior to water extraction | Post-extraction weight yield (from 5 g) | Viable cells (at 500 µg/mL) |
|---|---|---|
| 100:0 | 1.12 g | 76% |
| 80:20 (Lexirin) | 1.85 g | 83% |
| 60:40 | 2.33 g | 79% |
| 40:60 | 2.99 g | 73% |
| 20:80 | 3.63 g | 57% |
| 0:100 | 4.20 g | 46% |
| Untreated Control | N/A | 36% |

Results from in vitro anti-apoptosis assay testing (% of cells saved at a dose of 500 µg/mL) for Lexirin (lot 139–132) over a 6 month period under various storage conditions are shown in Table 6.

TABLE 6

Lexirin In vitro Activity During Storage

| Storage Conditions | Initial | 2 weeks | 1 month | 2 months | 3 months | 4 months | 6 months |
|---|---|---|---|---|---|---|---|
| 2–8° C. | | nt | nt | nt | nt | nt | 72% |
| Ambient | 82% | 76% | 86% | 85% | 82% | 83% | 72% |
| 34–38° C. | | nt | nt | nt | nt | nt | 71% | nt = not tested

EXAMPLE 5

In Vivo Studies

A. Animal Experiments

Animal experiments were performed as described previously in Funk-Archuletta, *Nutrition and Cancer* et al., *supra*. Briefly, 24 male Sprague-Dawley rats with an initial weight of approximately 200 grams were housed in individual wire-bottom stainless steel cages in a control environment with 12:12 hour light and dark cycle. Diets and water were provided ad libitum throughout the experiment. Rats were adapted to their diets for 7 days prior to methotrexate injection and remained on the diets for 7 days after the injection. Diets were formulated as follows:

1. Semi-purified diet with casein (20% of diet by dry weight);
2. Semi-purified diet with casein (10% of diet by dry weight) and ray soy flour (10% of diet by dry weight);
3. Semi-purified diet with casein and soy-derived anti-apoptotic fraction (SDAAF) (1.64% of diet by dry weight); and
4. Semi-purified diet with casein and soy water extract (Lexirin) (1.64% of diet by dry weight).

The level of the soy-derived anti-apoptotic fraction was chosen based on the previous study that demonstrated most favorable for such parameters as rat weight, food intake, and incidence of diarrhea (Funk-Archuletta et al., *Nutrition and Cancer, supra*).

Each diet group contained 6 rats. Duodenal tissue sections were taken from one rat of each diet group on day 0 (injection day) prior to methotrexate infection as a negative control. Remaining rates were injected IP with 20 mg/kg methotrexate (Sigma, St. Louis, MO) dissolved in phosphate buffered saline (PBS), pH 7.2. Duodenal sections of animals from each group were taken on days 2 and 5 after injection to evaluate dietary alleviation of methotrexate effect on duodenal mucosa. Animals were sacrificed by asphyxiation in a $CO_2$ chamber. Immediately after respiratory arrest rates were placed in a supine position and their thorax was opened to access the heart. Perfusion with 1000 units of heparin in 100 ml of 1×phosphate buffered saline, pH 7.2, was performed through te left ventricle while the right atrium was cut open for drainage. Perfusion with 4% formaldehyde in 1×phosphate buffered saline, pH.7.2, was performed using the same puncture on the left ventricle (*Current Methods of Molecular Biology*, vol. 2, sec. 14-1, John Wiley & Sons, 1996).

Following perfusion, rates were opened with a midline incision, and peritoneal cavity organs were grossly examined. Intestinal samples distal to the pyloric sphincter were then removed and placed in 4% formaldehyde for 24 hours fixation at 4° C. Tissues were processed for histopathological evaluation, embedded in paraffin, and cut into 5 µm sections on a microtome prior to hematoxylin and eosin staining. Histology of the duodenum and ileum was analyzed prior to methotrexate administration (day 0) and 4 hours after the injection (day 2) and 120 hours after the injection (day 5).

Samples were evaluated for alterations in muscosal structure, such as mucosal edema, villus degeneration and sloughed epithelium, cystic necrosis in crypts, crypt debris, and cytoplasmic vacuolization of crypt epithelium. Semi-quantitative analysis was performed for the following parameters: intestinal villi height (in % compared to non-treated control on standard rate foot diet); intestinal crypt mitosis absolute number of mitotic figures per crypt sectioned vertically); shortened intestinal epithelium (1–2—slight, 3–4—moderate, 5–6—strong); and cellular infiltration as an inflammatory response (polymorphonuclear leucocytes, macrophages, lymphocytes) (1–2—slight, 3–4—mild, 5–6—moderate 7–8—strong).

B. Gross Findings

The gross findings on laparotomy in the casein diet group were as previously reported in Robinson et al., *Biomet*

*Pharmacology*, 15:1479–1489 (1966), and included distention of the stomach and small intestine. 48 hours after methotrexate injection, the small intestine was dilated about twice the normal size and significantly shortened with much thinner intestinal walls. Similar changes (to a lesser extent) were observed in the raw soy flour and soy fraction diet groups within 48 hours of methotrexate injection. At 120 hours (day 5) the diameter of the small intestine was increased in all diet groups. In the casein diet group, duodenal dilation was more pronounced while in the soy derived diets intestinal walls remained of normal width.

C. Histological Analysis

Histology of the duodenum and ileum was analyzed prior to methotrexate administration (day 0) and at 48 (day 2) and 120 hours (day 5) post methotrexate administration. Duodenal and jejunal sections taken at these time points showed pronounced changes following methotrexate administration. Lesser histological changes were found in ileum and colon samples.

Day 0

On day 0, the morphology of all duodenum/jejunum samples appeared normal; slight inflammatory cellular infiltrate and somewhat shortened villi were noted; in the raw soy flour and in the soy-derivative groups mild villi hyperplasia was observed compared to casein based diets.

Day 2 (48 hours Post Methotrexate Administration)

In the casein diet group there was severe necrosis and villi degeneration as previously reported in Funk & Baker, *J. Nutr.*, 121:1584–1692 1991 and Robinson et al., *supra*. Intestinal villi were notably flattened (Table 7), and mitotic arrest in the crypts led to a significant decrease of observable number of the mitotic figures (Table 8). Additionally, vacuolization and nuclear pyknosis were noted in the remaining crypt cells, with many crypts demonstrating cystic degeneration. Mature intestinal epithelial cells were shortened (Table 9) and patches of complete desquamation were found in several areas of the duodenum. Severe cellular infiltration was observed in the entire lamina propria (Table 10).

In the raw soy diet and in the soy-derived diet groups, necrotic and apoptotic damage was markedly reduced. Villi were shortened to a lesser degree, while the crypts retained some mitotic activity, and cystic degeneration was less evident. The intestinal epithelium appeared normal in most areas and slightly shortened in some patches; cellular infiltration of the lamina propria was less evident. Variations between the raw soy and anti-apoptotic derivative diets, as shown in Tables 7–10, indicate duodena of animals treated with SDAAF and Lexirin had longer villi, higher mitotic activity and less changes in duodenal epithelial cells.

TABLE 7

In vivo histological analysis from rat methotrexate study
Villi Height

| | Days Post MTX Treatment | | |
|---|---|---|---|
| Diet | 0 | 2 | 5 |
| Casein | 85 | 30 | 20 |
| Raw Soy Flour | 100 | 40 | 95 |
| SDAAF | 95 | 50 | 80 |
| Lexirin | 95 | 45 | 80 |

Histological analysis of intestinal villi height following Methotrexate (MTX) treatment on Day 0. Villi height is expressed as percent compared to non-treated control rats fed standard diet.

TABLE 8

Intestinal Crypt Cell Mitosis

| | Days Post MTX Treatment | | |
|---|---|---|---|
| Diet | 0 | 2 | 5 |
| Casein | 4 | 0.1 | 4 |
| Raw Soy Flour | 8 | 3 | 8 |
| SDAAF | 9 | 6 | 8 |
| Lexirin | 7 | 5 | 9 |

Histological analysis of intestinal crypt cell mitosis following Methotrexate (MTX) treatment on Day 0. Values are expressed as averages of the absolute number of mitotic figures per vertically-sectioned crypt.

TABLE 9

Shortened Intestinal Epithelium

| | Days Post MTX Treatment | | |
|---|---|---|---|
| Diet | 0 | 2 | 5 |
| Casein | 0 | 3 | 6 |
| Raw Soy Flour | 0 | 1.5 | 0 |
| SDAAF | 0 | 1.5 | 0 |
| Lexirin | 0 | 1.5 | 0 |

Histological analysis of shortened intestinal epithelium following Metotrexate (MTX) treatment on Day 0. Incidence of shortened intestinal epithelium is scored as follows: 1–2 slight; 3–4 moderate; 5–6 strong.

TABLE 10

Cellular Infiltration

| | Days Post MTX Treatment | | |
|---|---|---|---|
| Diet | 0 | 2 | 5 |
| Casein | 3 | 7 | 8 |
| Raw Soy Flour | 1 | 5 | 1 |
| SDAAF | 2 | 6 | 2 |
| Lexirin | 2 | 5 | 2 |

Histological analysis of cellular infiltration following Methotrexate (MTX) treatment on Day 0. Analyzed in terms of inflammatory response (evidence of polymorphnuclear leucocytes, macrophages, lymphocytes) and scored as follows: 1–2 slight; 3–4 mild; 5–6 moderate; 7–8 strong.

Day 5 (120 Hours Post Methotrexate Administration)

In the casein diet group the duodenal and jejunal epithelium had completely disappeared, showing only small areas with shortened epithelial cells. Villi were even more damaged than on day 2, and cellular infiltration of the lamina propria remained severe. However, mitotic activity within crypts started to recover as shown in Table 7.

In the raw soy four diet group, intestinal villi returned to their normal height, and enterocytes appeared morphologically normal. The number of mitotic figures in the crypts exceeded the initial number present prior to administration, possibly as a compensatory reaction to methotrexate treatment; mild cellular infiltration of the lamina propria was still present.

A similar rapid recovery was found in SDAAF and Lexirin diet groups where villi were slightly shorter and the number of mitotic figures was higher than that seen in the raw soy flour diet group. In general, raw soy flour and soy derived anti-apoptotic diets markedly reduced apoptosis in villi epithelium and necrotic damage in the crypts.

The protection of mucosal integrity by SDAAF and Lexirin was evident as shown by greater villus height and mitotic activity as well as lower incidence of crypt apoptosis, cellular infiltrate, and shortened epithelial cells. Damage to casein-fed animals and protection by raw soy flour, SDAAF and Lexirin was most evident in the upper small intestine. Gross and histological findings 48 hours after MTX injection demonstrated severe necrosis, and villi degeneration in casein-fed animals, while in raw soy flour, Lexirin and SDAAF diet groups duodenal villi were shortened to a lesser degree, the crypts retained some mitotic activity, and cystic degeneration was less evident. At 120 hours the duodenal epithelium of casein-fed animals demonstrated even worse damage, with marked cellular infiltration displayed the beginning of mitotic recovery within the crypts. In raw soy flour, Lexirin and SDAAF diet groups intestinal villi were close to their normal height, and enterocytes appeared morphologically normal; the number of mitotic figures in the crypts exceeded the initial mitosis number present prior to administration, possibly as a compensatory reaction to MTX treatment.

These results indicate that both Lexirin and SDAAF, when given at low, therapeutically feasible doses, have a similar protection effect against MTX-induced gastrointestinal toxicity as raw soy flour when given at much higher doses. In addition to chemotherapy-induced toxicity, treatment with ionizing radiation has been shown to induce apoptosis in jejunal crypt cells as reported in Weil et al., *Int. J. Radit. Biol.*, 70:579–585 (1996).

The difference in protease inhibitory activities between SDAAF and Lexirin while retaining anti-apoptotic activity suggests that this activity does not depend on the presence of the two major inhibitors present in soy: Kunitz trypsin inhibitor and Bowman Birk Inhibitor.

While various embodiments of the present invention have been described in detail, it is apparent that modifications and adaptations of those embodiments will occur to those skilled in the art. It is to be expressly understood, however, that such modifications and adaptations are with the scope of the present invention and are only limited by the following claims.

What is claimed is:

1. A method of treating or preventing a gastrointestinal disorder associated with apoptosis comprising administering a therapeutically effective amount of an anti-apoptotic composition to a mammal in need of treatment or prevention of an adverse condition associated with apoptosis, wherein said antiapoptotic composition is prepared by the steps of:

supplying a soy protein isolate and a soy lipid mixture (in a ratio of 4:1 protein isolate:lipid mixture) that has not been delipidated;

mixing said 4:1 soy protein isolate, soy lipid mixture in an aqueous solution not containing an organic solvent; and separating the aqueous solution from insoluble material, wherein said anti-apoptotic composition is present in said aqueous solution.

2. The method of claim 1, wherein said gastrointestinal disorder is diarrhea.

* * * * *